(12) United States Patent
Cygan et al.

(10) Patent No.: US 12,409,363 B2
(45) Date of Patent: Sep. 9, 2025

(54) NORMALIZED ISOKINETIC STRENGTH TRAINING PERFORMANCE AND PRESCRIPTION

(71) Applicant: Gymbot, LLC, Lake Zurich, IL (US)

(72) Inventors: Brian Cygan, Wauconda, IL (US); Bradley Bundy, Montgomery, TX (US); Kurt Pinnow, Rochester, MN (US)

(73) Assignee: GYMBOT, LLC, Lake Zurich, IL (US)

( * ) Notice: Subject to any disclaimer, the term of this patent is extended or adjusted under 35 U.S.C. 154(b) by 143 days.

(21) Appl. No.: 18/369,808

(22) Filed: Sep. 18, 2023

(65) Prior Publication Data

US 2024/0091591 A1 Mar. 21, 2024

Related U.S. Application Data

(60) Provisional application No. 63/407,691, filed on Sep. 18, 2022.

(51) Int. Cl.
*A63B 24/00* (2006.01)
(52) U.S. Cl.
CPC ...... *A63B 24/0062* (2013.01); *A63B 24/0087* (2013.01); *A63B 2024/0065* (2013.01);
(Continued)
(58) Field of Classification Search
CPC ............ A63B 24/0062; A63B 24/0087; A63B 2024/0065; A63B 2024/0071;
(Continued)

(56) References Cited

U.S. PATENT DOCUMENTS

| | | | | |
|---|---|---|---|---|
| 5,054,774 A | * | 10/1991 | Belsito | A63B 24/00 |
| | | | | 715/784 |
| 6,227,047 B1 | * | 5/2001 | Livingston | G16H 20/30 |
| | | | | 73/379.08 |

(Continued)

OTHER PUBLICATIONS

PCT/US2023/033089. International Search Report & Written Opinion (Dec. 12, 2023).

*Primary Examiner* — Sundhara M Ganesan
(74) *Attorney, Agent, or Firm* — Heidi Eisenhut; LOZA & LOZA, LLP

(57) ABSTRACT

Embodiments of the present disclosure are directed to a computer system of an exercise machine for maximizing muscle recruitment through capability based concentric and eccentric training. The system includes a communication interface; at least one processor, operatively coupled to the communication interface; at least one computer readable memory having a non-transitory computer-readable storage medium configured to store instructions, that when executed by the processor are configured to establish a machine set-up, on the exercise machine, consistent with joint angle standards for a dynamic isokinetic resistance exercise on the exercise machine; establish a machine position, on the exercise machine, for a prescribed joint angle position during an isometric force production evaluation exercise performed on the exercise machine; calculate a maximum isometric effort at a prescribed joint angle for one or more exercises performed on the exercise machine; and calculate a baseline resistance level for at least one protocol.

11 Claims, 11 Drawing Sheets

(52) U.S. Cl.
CPC ............. *A63B 2024/0071* (2013.01); *A63B 2024/0093* (2013.01); *A63B 2220/17* (2013.01); *A63B 2220/20* (2013.01); *A63B 2220/30* (2013.01); *A63B 2220/51* (2013.01); *A63B 2220/62* (2013.01)

(58) Field of Classification Search
CPC ........ A63B 2024/0093; A63B 2220/17; A63B 2220/20; A63B 2220/30; A63B 2220/51; A63B 2220/62; A63B 23/0417; A63B 2071/0658; A61B 5/4519; A61B 5/4836; A61B 5/6895; A61B 5/742; A61B 5/224; A61B 5/222; A61B 2503/10; A61B 2503/12
See application file for complete search history.

(56) References Cited

U.S. PATENT DOCUMENTS

| | | | |
|---|---|---|---|
| 6,436,006 B1 * | 8/2002 | Zemlyakov | A63B 21/155 482/112 |
| 9,868,025 B2 * | 1/2018 | Cygan | A63B 21/4047 |
| 10,843,041 B1 * | 11/2020 | Cobb | A63B 21/0428 |
| 11,458,354 B2 * | 10/2022 | Bissonnette | A63B 23/03516 |
| 11,596,837 B1 * | 3/2023 | Belson | A63B 24/0087 |
| 2004/0248713 A1 | 12/2004 | Campanaro et al. | |
| 2007/0202992 A1 * | 8/2007 | Grasshoff | A63B 24/00 482/8 |
| 2015/0258384 A1 * | 9/2015 | Suzuki | A63B 24/0087 482/5 |
| 2016/0059077 A1 * | 3/2016 | Paul | A63B 21/002 482/4 |
| 2016/0114211 A1 * | 4/2016 | Schmidt | A63B 21/4043 482/8 |
| 2017/0282015 A1 * | 10/2017 | Wicks | A63B 24/0075 |
| 2017/0319941 A1 | 11/2017 | Smith et al. | |
| 2017/0361165 A1 * | 12/2017 | Miller | A63B 21/4047 |
| 2018/0001181 A1 * | 1/2018 | Von Prellwitz | A63B 24/0075 |
| 2019/0021929 A1 | 1/2019 | Einav et al. | |
| 2019/0046830 A1 | 2/2019 | Chiavegato et al. | |
| 2020/0261771 A1 * | 8/2020 | Belson | A63B 24/0062 |
| 2021/0268332 A1 * | 9/2021 | Smith | A61B 5/22 |
| 2021/0394011 A1 * | 12/2021 | Neuhaus | A63B 71/0622 |
| 2022/0197380 A1 | 6/2022 | Tokubo et al. | |
| 2022/0314077 A1 * | 10/2022 | Bissonnette | A63B 24/0075 |

\* cited by examiner

CHOOSE PROTOCOL

- STANDARD
- BUILD
- SHIFT
- REV (402)
- RELEASE
- FOCUS

- DIG
- PEAK
- REACH
- ACCOMMODATE
- UTILITY
- CUSTOM

CHOOSE TARGET BASE

PROTOCOL BASED

| | date | protocol | strength index | total effort |
|---|---|---|---|---|
| BEST | 06/24/22 | REV | 267 | 8153 |
| LAST | 06/24/22 | REV | 267 | 8153 |

ADJUST TARGET
Strength Index 306    [ - ]    Percent: 0%

MOVEMENT BASED

| | date | protocol | index | effort |
|---|---|---|---|---|
| BEST | 08/21/22 | Ecc3 | 307 | 8865 |
| LAST | 09/10/22 | All-out | 306 | 8444 |

9333 Target Effort    [ + ]

[Perform Exercise]   [Back]

*FIG. 4*

NORMALIZED ISOKINETIC STRENGTH TRAINING PERFORMANCE AND PRESCRIPTION

CLAIM OF PRIORITY

This application claims priority to and the benefit of U.S. Provisional Patent Application No. 63/407,691, titled NORMALIZED ISOKINETIC STRENGTH TRAINING PERFORMANCE AND PRESCRIPTION, and filed on Sep. 18, 2022, at the United States Patent and Trademark Office, the entire content of which is incorporated by reference herein as if fully set forth below in its entirety for all applicable purposes.

FIELD

The present invention relates to measuring the muscular performance, including strength and endurance, generated upon completion of an exercise set that maximizes muscle recruitment through capability based concentric and eccentric training.

BACKGROUND

Isometric evaluation in the fitness industry refers to the assessment of muscular strength and endurance through isometric exercises. Isometric exercises are a type of strength training in which the muscle contracts without changing its length, meaning there is no visible movement at the joint. Instead, the muscle exerts force against an immovable object or resists an opposing force.

To evaluate an individual's isometric strength and endurance, a specific exercise or set of exercises is chosen for each muscle group being assessed. Common isometric exercises include wall sits, planks, and static holds with resistance bands or machines. During the isometric exercise, the participant exerts maximal force against an immovable object, such as pushing against a wall or holding a position against resistance. The amount of force generated by the muscle is measured using specialized equipment like dynamometers or force plates. Alternatively, trainers can use subjective scales, such as the Borg Rating of Perceived Exertion (RPE), to gauge the perceived effort and fatigue.

The individual typically holds the isometric position for a specific duration, often measured in seconds or minutes. The duration may vary depending on the goals of the assessment, with longer holds assessing endurance and shorter holds assessing maximal strength. Multiple repetitions of the isometric exercise may be performed with short rest intervals in between to assess the muscle's endurance capacity. The total time under tension can also be recorded.

Data collected during the isometric evaluation includes the maximum force exerted, time held, and any subjective ratings of discomfort or fatigue. This information helps trainers and fitness professionals tailor exercise programs to the individual's needs. The collected data is analyzed to assess the participant's muscle strength and endurance. Comparisons can be made to normative data or previous assessments to track progress over time. Based on the assessment results, fitness professionals can design personalized workout programs that target specific muscle groups or weaknesses. Isometric exercises may be incorporated into the training regimen to improve strength and endurance where needed.

Isometric evaluation has several benefits. It provides objective data on an individual's muscular strength and endurance, allowing for a more precise understanding of their fitness level. Results from isometric evaluations help design customized training programs that address specific weaknesses or imbalances in muscle groups. Regular assessments enable clients to track their progress over time, motivating them to continue their fitness journey. Identifying muscle weaknesses or imbalances can help prevent injuries by addressing potential problem areas through targeted exercises.

Overall, isometric evaluation is a valuable tool in the fitness industry for assessing and improving muscular strength and endurance, ultimately helping individuals achieve their fitness goals in a safe and effective manner.

BRIEF SUMMARY

The following presents a simplified summary of one or more aspects of the present disclosure to provide a basic understanding of such aspects. This summary is not an extensive overview of all contemplated features of the disclosure. It is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description presented below.

In one example, a computer system of an exercise machine for maximizing muscle recruitment through capability based concentric and eccentric training is provided. The computer system includes a communication interface; at least one processor, operatively coupled to the communication interface; and at least one computer readable memory configured to communicate with the at least one processor, the computer readable memory having a non-transitory computer-readable storage medium configured to store instructions. When the stored instructions are executed by the at least one processor are configured to establish a machine set-up, on the exercise machine, consistent with joint angle standards for a dynamic isokinetic resistance exercise on the exercise machine; establish a machine position, on the exercise machine, for a prescribed joint angle position during an isometric force production evaluation exercise performed on the exercise machine; calculate a maximum isometric effort at a prescribed joint angle for one or more exercises performed on the exercise machine; and calculate a baseline resistance level for at least one protocol.

According to one aspect, the baseline resistance level is calculated using a combination of data obtained from an isometric evaluation and a user performance of an exercise set on the exercise machine.

According to another aspect, the data includes an exercise performed, a range of motion, a duration of repetition, a duration of set, a number of repetitions, a number of sets, a tempo of repetitions, a total effort, an average effort, a peak concentric force, an average concentric force, a peak eccentric force, and an average eccentric force.

According to yet another aspect, the at least one protocol comprises one or more distinct prescriptive variables.

According to yet another aspect, the one or more distinct prescriptive variables include a time under load, a speed of movement, a concentric loading, and an eccentric loading.

According to yet another aspect, wherein the at least one processor is further configured to normalize the data of the user performance to provide an accurate analysis of current strength levels of a user allowing for the user performance to be compared across different protocols.

According to yet another aspect, the at least one processor is further configured to display a visual target on a display screen, the visual target provides real time feedback to a user.

According to yet another aspect, the visual target is a resistance curve that is biomechanically congruent with each movement of the user based on a standardized range of motion used to maximize safety and effectiveness on the each movement.

According to yet another aspect, the at least one processor is further configured to convert a total effort recorded for a baseline dynamic exercise set performed on the exercise machine into a value that is a predicted isometric maximum test value.

According to yet another aspect, the at least one processor is further configured to normalize the total effort recorded for the at least one protocol performed on the exercise machine using the predicted isometric maximum test value.

According to yet another aspect, the at least one processor is further configured to display a normalized total effort recorded for the at least one protocol performed on the exercise machine.

According to another example, a method of maximizing muscle recruitment through capability based concentric and eccentric training is provided. The method includes establishing a machine set-up, on the exercise machine, consistent with joint angle standards for a dynamic isokinetic resistance exercise on the exercise machine; establishing a machine position, on the exercise machine, for a prescribed joint angle position during an isometric force production evaluation exercise performed on the exercise machine; calculating a maximum isometric effort at a prescribed joint angle for one or more exercises performed on the exercise machine; and calculating a baseline resistance level for at least one protocol.

According to one aspect, the baseline resistance level is calculated using a combination of data obtained from an isometric evaluation and a user performance of an exercise set on the exercise machine.

According to another aspect, the at least one protocol comprises one or more distinct prescriptive variables; and wherein the one or more distinct prescriptive variables include a time under load, a speed of movement, a concentric loading, and an eccentric loading.

According to yet another aspect, the method further comprises normalizing the data of the user performance to provide an accurate analysis of current strength levels of a user allowing for the user performance to be compared across different protocols; displaying a visual target on a display screen, the visual target provides real time feedback to a user; and converting a total effort recorded for a baseline dynamic exercise set performed on the exercise machine into a value that is a predicted isometric maximum test value.

BRIEF DESCRIPTION OF THE DRAWINGS

The features, nature, and advantages of the present aspects may become more apparent from the detailed description set forth below when taken in conjunction with the drawings in which like reference characters identify correspondingly throughout.

FIG. 4 illustrates a display screen showing different protocols that may be selected for any movement or exercise, according to one aspect.

DETAILED DESCRIPTION OF THE INVENTION

Figure 1:
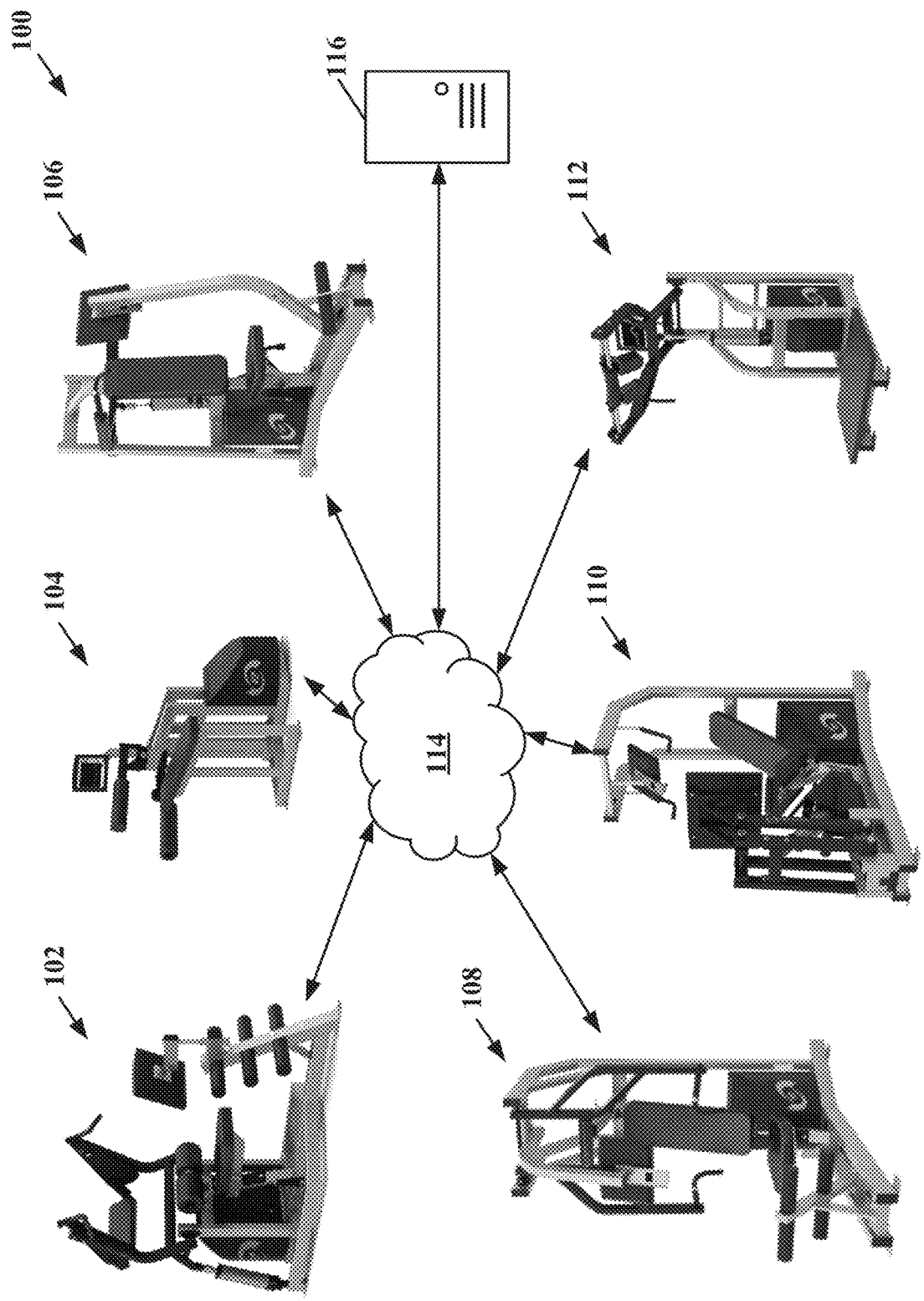
FIG. 1 illustrates a plurality of exercise machines connected to a server through a communications network.

In the following description, specific details are given to provide a thorough understanding of the embodiments. However, it will be understood by one of ordinary skill in the art that the embodiments may be practiced without these specific details.

Terms

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise. The word "exemplary" is used herein to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage, or mode of operation.

The terms "user" and "individual" may be used interchangeably.

The term "iso-velocity technology", developed by Applicant, refers to Multi-Joint Technology that allows concentric and eccentric muscle contractions at a constant rate of speed and increases the load as it senses that the muscle contraction is strengthening and speeding up. Iso-velocity technology provides for muscle gaining strength faster than traditional methods and more evenly throughout the entire range of movement. Iso-velocity technology measures accurate force output from all users, that is, from elite athletes to people who have lost motor control due to partial paralysis. Based on the customized strength profile of each user, a custom training protocol can be controlled and documented.

Due to training to an individual's capability, the central nervous system is engaged more effectively than with traditional training.

The terms "concentric" and "concentric loading" refer to the phase of a muscle contraction where the muscle shortens while generating force against resistance. This is the most common and well-known phase of a resistance exercise and is often referred to as the "lifting" or "positive" phase. During concentric loading, the muscle overcomes the resistance, causing joint movement and muscle contraction.

The terms "eccentric" and "eccentric loading" refer to the phase of a muscle contraction where the muscle lengthens while under tension. This phase is often referred to as the "negative" phase and is the opposite of concentric loading, where the muscle shortens while generating force.

The term "dynamic isokinetic resistance exercise" is a general description of the type of dynamic (with movement) exercise that is performed. An isometric force production evaluation exercise will involve the same exercise "movement" however it will be performed with the machine in a static position so that no movement really occurs but instead the user presses against the immovable work arm of the machine (the motor locks it in place). This is an isometric procedure. There is no movement and the force against the machine generated by the user is recorded.

The term "strength level" refers to an individual's ability to generate force against resistance. It is a measure of how much weight or resistance a person can lift, push, or pull in relation to their body weight or other factors.

The term "protocols" refers to coded parameters that determine the prescriptive variables applied to an exercise like speed of movement in each direction and number of repetitions.

"Exerbotics®", developed by Applicant, refers to providing a tool, such as exercise equipment, to maximize muscle recruitment through capability based concentric and eccentric training. Exerbotics® scientifically assesses and trains the human body as the exercise equipment reacts to the individual, regardless of personal limitations or abilities.

An Exerbotics® strength assessment test measures force or effort supplied by the user, significantly increasing safety during maximum efforts. By utilizing the iso-velocity technology which can measure multi-joint, compound movements, tests are administered and recorded in a computer-controlled environment, eliminating external elements such as technique, inertia, speed, and range of motion; all of which can skew results. Exerbotics® includes a precision load cell as part of its iso-velocity technology to measure an individual's force output throughout the range of motion. The computer and load cell may take 514 measurements per direction, according to one example, to accurately document an individual's concentric and eccentric strength curve. That is 1,028 data points for each repetition. Exerbotics® fitness testing equipment offers the strength assessment and training advantages required in a multitude of applications including corporate wellness, athletics, rehabilitation, active aging, and general fitness.

Information and data gathered using iso-velocity software includes, but is not limited to, exercise performed, range of motion, duration of repetition, duration of set, number of repetitions, number of sets, tempo of repetitions, total effort, average effort, peak concentric force, average concentric force, peak eccentric force, and average eccentric force.

The term "strength index" refers to a measurement of a muscular performance (strength and endurance) that is generated upon completion of an Exerbotics® Movement Protocol (in other words an exercise set using Exerbotics®). This measurement can provide performance comparisons between different protocols and is also used to evaluate progress over time relative to a baseline measurement or a baseline resistance level. Strength index may be used in the development of age-matched benchmarks and reference ranges for healthy muscular function.

Utilizing strength index involves using normalized data or optimized coaching. Data normalization is the process of adjusting values measured on different scales to a theoretically common scale. Protocols are used for performing exercise sets. Each individual protocol is made up of distinct prescriptive variables including time under load, speed of movement, emphasis on concentric vs. eccentric loading, etc. Each individual protocol is different and distinct. By utilizing data normalization, it is possible to compare the performance of a user/individual across any given protocol as the measurement is made common across the distinctly different protocols. By normalizing the data, fast and accurate analysis of current strength levels can be obtained.

To use data normalization, a baseline for the user/individual is first obtained. The baseline allows for the immediate optimal muscular stimulation and the work that the user/individual performs to be efficacious from the beginning. This provides for better strength gains and better strength over time through smart informed coaching and progression and consistent performance assessment across various protocols. This, in turn, leads to progress analysis that is based on all the protocol performances that are easy to understand.

At the beginning of the process to establish a new baseline, the rotations per minute (RPM) process in conjunction with strength index is used. The range of motion setup and isometric evaluation is used. After, the isometric evaluation (or max test) is followed by an exercise set. Unlike the prior art, the isometric evaluation is not relied on solely to create a baseline. A combination of information or data obtained from the isometric evaluation and what the user/individual can perform (i.e., a user's performance) on his or her first exercise set, based on that isometric evaluation, provides a much more personalized and accurate baseline. Once the isometric evaluation has been completed, the type of performance is selected. The type of performance is selected between standard performance and accommodate performance and the first exercise set is performed.

Once a set of a standard or accommodate performance has been completed, the system and methods of the present disclosure will calculate the user/individual's baseline, the baseline may be different than the isometric value. Some adjustments may be required based on the data to provide the most accurate and the most appropriate baseline. So, for some users, their baseline might be slightly higher than the isometric value or for some, it might be slightly lower, but that will be the baseline going forward. As a result, no additional isometric evaluation will be required on the user to provide a progress update, or to adjust targeting on any new protocols as the baseline has been determined.

Turning to FIG. 1, a plurality of exercise machines (or exercise devices) 102-112 connected to a server 116 through a communications network 114 is shown. The plurality of machines (or exercise devices) 102-112 may include, but are not limited to, a back machine 102, a contralateral hamstring machine 104, a shoulder press/pull down machine 106, a chest press/row machine 108, a leg press machine 110, and a squat machine 112. As described in more detail below, each of the exercise machines (or exercise devices) may include a communication interface, such as a transceiver, and at least one processor, operatively coupled to the communication interface. Each of the exercise machines may further include a computer system having at least one computer readable memory, having a non-transitory computer-readable storage medium configured to store instructions, and configured to communicate with the at least one processor. The communication interface in the exercise machine is configured to communicate with the server and/or other exercise machines in the plurality of exercise machines.

Figure 2:
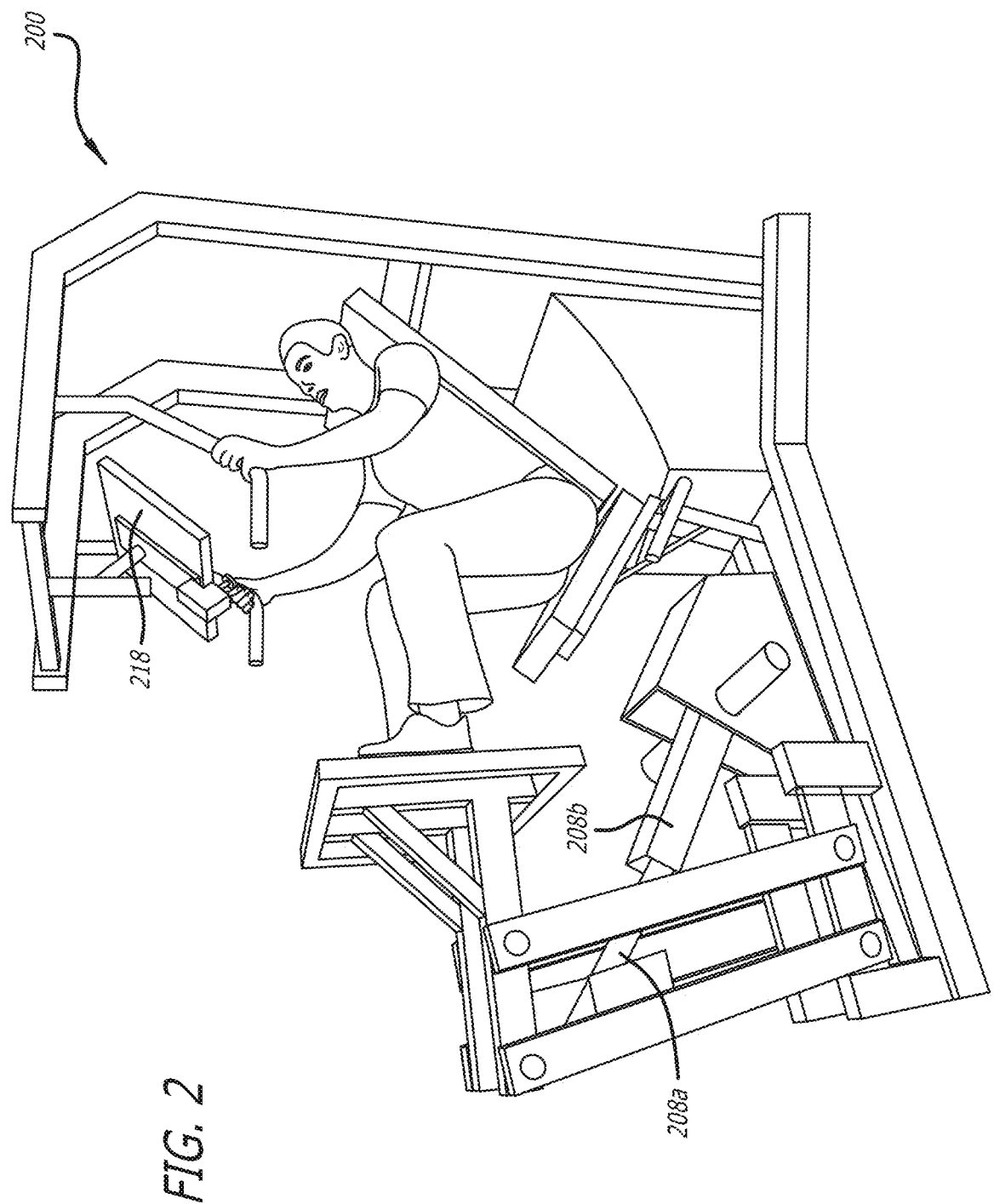
FIG. 2 illustrates an individual utilizing a leg press machine, according to one aspect.

FIG. 2 illustrates an individual utilizing a leg press machine 200, in accordance with an aspect of the present disclosure. As described above with reference to FIG. 1, the leg press machine 200 may communicate with a server and/or other exercise machines. As shown, a 90-degree joint angle position is obtained during an isometric force production evaluation. The leg press machine utilizes a motor secured to, and in electrical communication with, a linear actuator having a cylinder 208b and a piston 208a axially engaged with the cylinder 208b. The leg press machine 200 may include a display 218 for displaying various information to the individual and/or coach/trainer working with the individual. The information may include, but is not limited to, protocol selected/utilized, exercise performed, range of motion, duration of repetition, duration of set, number of repetitions, number of sets, tempo of repetitions, total effort, average effort, peak concentric force, average concentric force, peak eccentric force, and average eccentric force.

Figure 3:
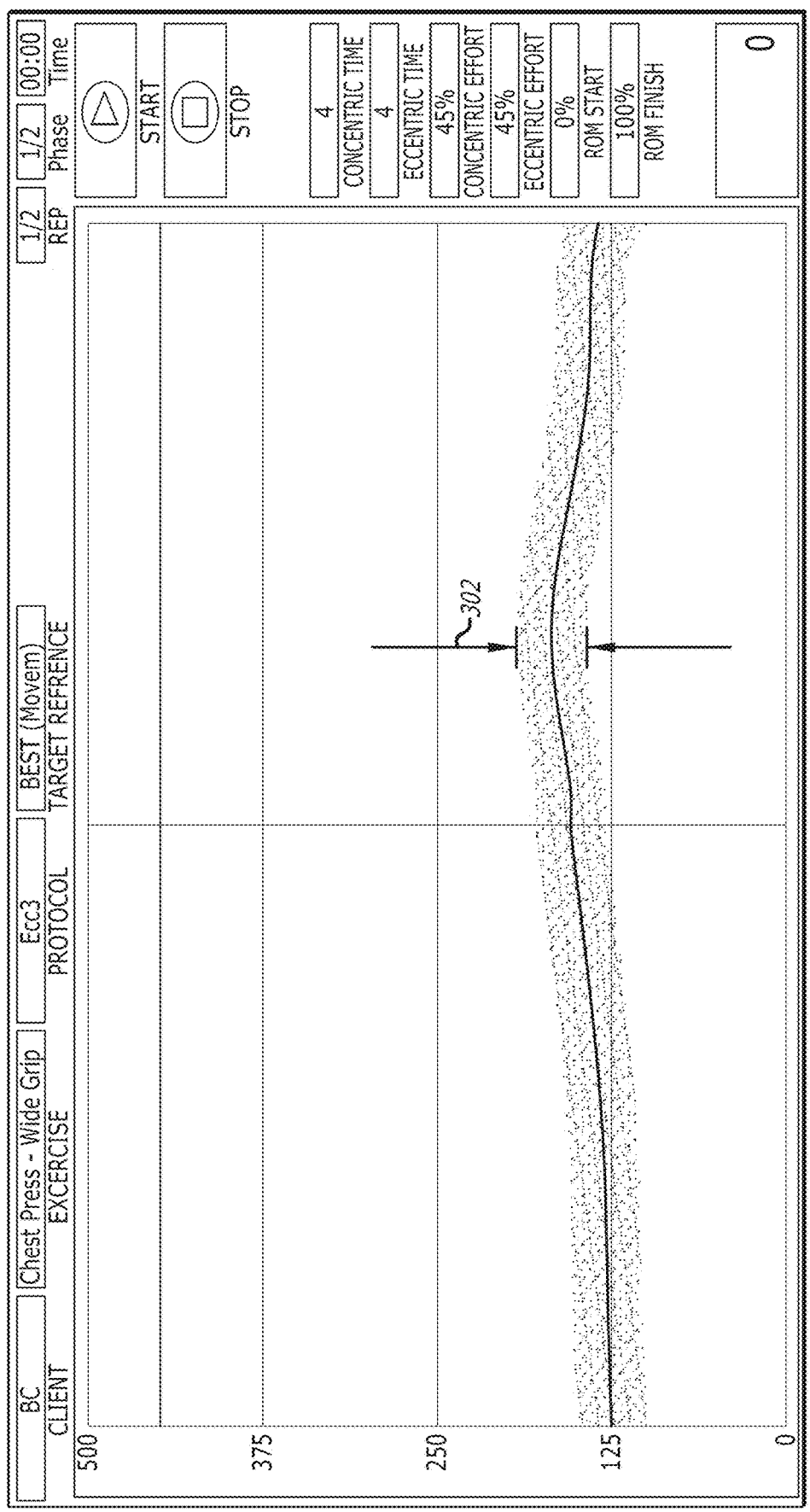
FIG. 3 illustrates a display screen showing the force being applied by an individual in real time compared to a visual target according to one.

FIG. 3 illustrates an example of a display screen on an exercise machine displaying the force being applied by an individual in real time compared to a visual target. The display shows the force being applied to an exercise machine, such as the leg press machine of FIG. 3. The visual target 302 is displayed on the monitor to provide real time feedback which guides and motivates individual exercise effort. Each visual target 302 involves a proprietary resistance curve that is biomechanically congruent with each movement based on the standardized range of motion used to maximize safety and effectiveness on each movement. This is only possible through an algorithm that requires the data from the isometric test performed at a prescribed joint angle.

FIG. 4 illustrates another example of a display screen showing different protocols that may be selected for any movement or exercise, using an exercise machine or device. This display screen allows the user/individual or coach/trainer to decide how to target or provide target effort for the user/individual for any movement or exercise which is the target basis using two different methods, a protocol-based method, and a movement-based method. Protocol-based targeting means looking at only performances or the protocol that will be performed. Protocols, which are well known in the art may be selected. According to one aspect, the protocols may include, but are not limited to, standard, build, shift, REV (i.e., revs the heart), release, focus, DIG, peak, reach, accommodate, utility, and custom.

Using this display screen, the user/individual, or coach/trainer, can select the protocol 402 to utilize. For example, if the REV protocol is selected on a chest press, protocol-based targeting is utilized. After selecting the REV protocol, only REV protocol performances, either the best or last target base may be selected. That is, either the best target base or the last target base that was performed is selected. Once the protocol is selected, the target can be increased which will increase the strength index target for a particular exercise. Alternatively, the target can be decreased which will decrease the strength index target for a particular exercise.

Figure 5:
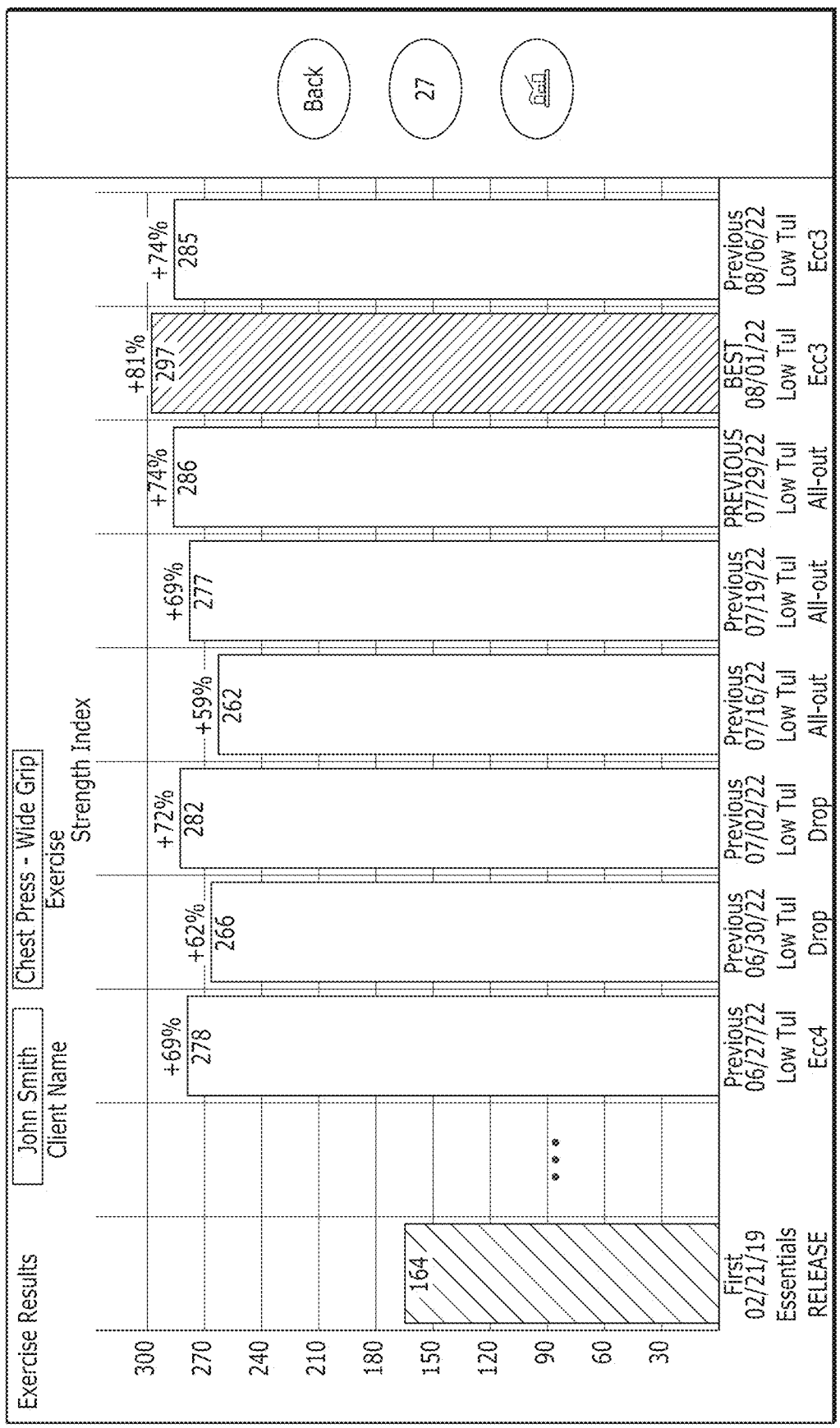
FIG. 5 illustrates a display screen showing a movement performance review for movement-based targeting when an exercise set has been completed, according to one aspect.
Figure 6:
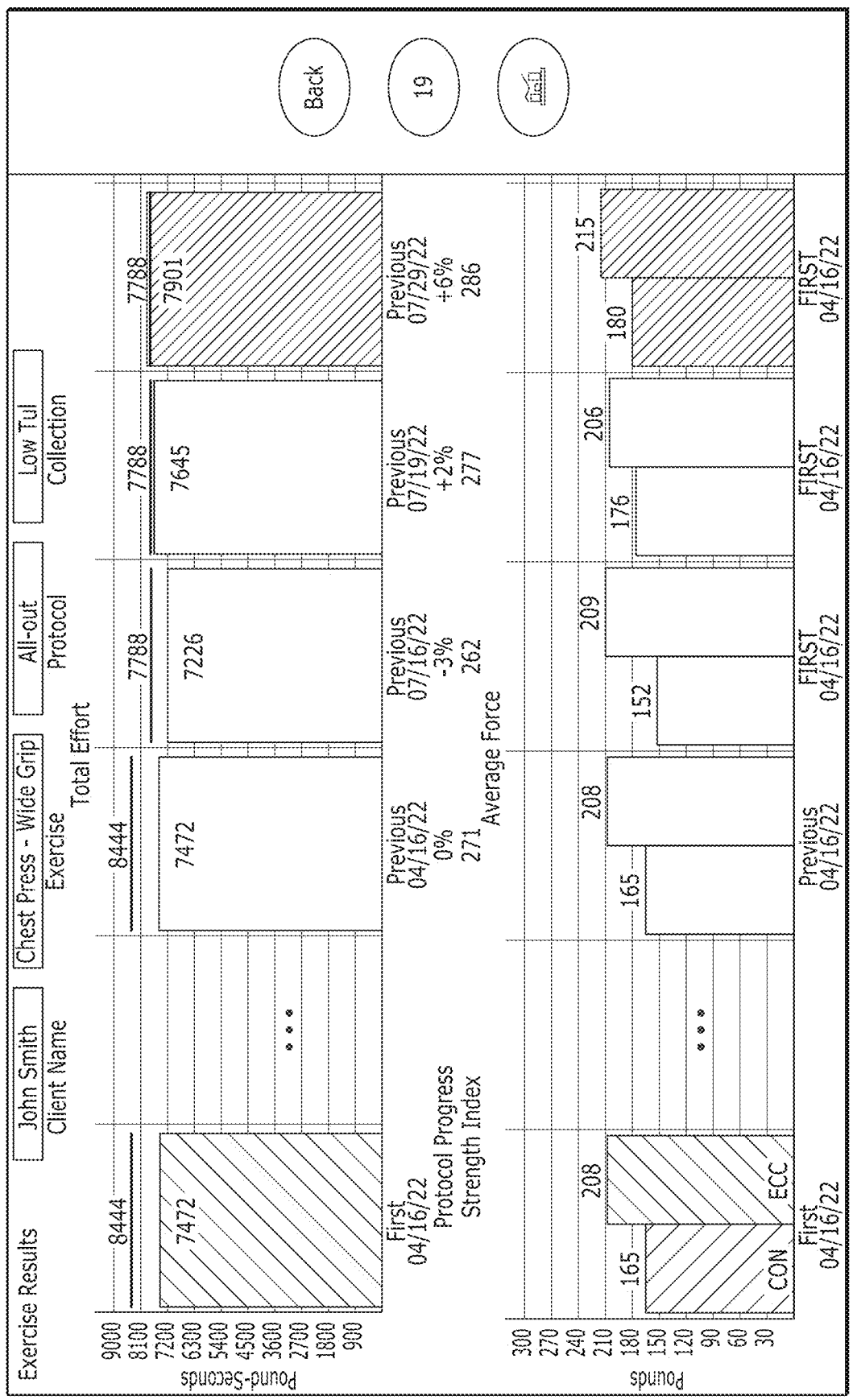
FIG. 6 illustrates a display screen showing how the user/individual performed on the different protocols through the lens of a common metric, a common analysis, according to one aspect.

If movement-based targeting is selected, the best or last performance across any protocol that the user/individual has performed across the whole movement is selected. So, if the user/individual has performed five or six or seven different protocols, a selection is made from all those protocols to show the best strength index the user/individual has generated and the protocol that was performed on, or the last performance the user/individual had on the movement. At the completion of an exercise set, results screens are generated for the user/individual. FIGS. 5 and 6 illustrate example results screens generated after the completion of an exercise set.

FIG. 5 illustrates a display screen showing a movement performance review for movement-based targeting when an exercise set has been completed, according to one aspect. As shown in this example, a chest press—wide grip exercise has been selected. The screen shows the strength index compared to a baseline and percentage gain or change across all the different protocols for a given movement, all the protocols that have been performed, it does not matter if different protocols are being performed, strength index is a normalized metric.

FIG. 6 illustrates a display screen showing how the user/individual performed on the different protocols through the lens of a common metric, a common analysis, according to one aspect. As shown in this example, a chest press—wide grip exercise has been selected. This provides for showing the meaningful progress of the user/individual even though different protocols were used, strength index is what makes that possible through that normalized data. In this example, the total effort, as well as the average force, on the chest press—wide grip on different days is shown.

Figure 7:
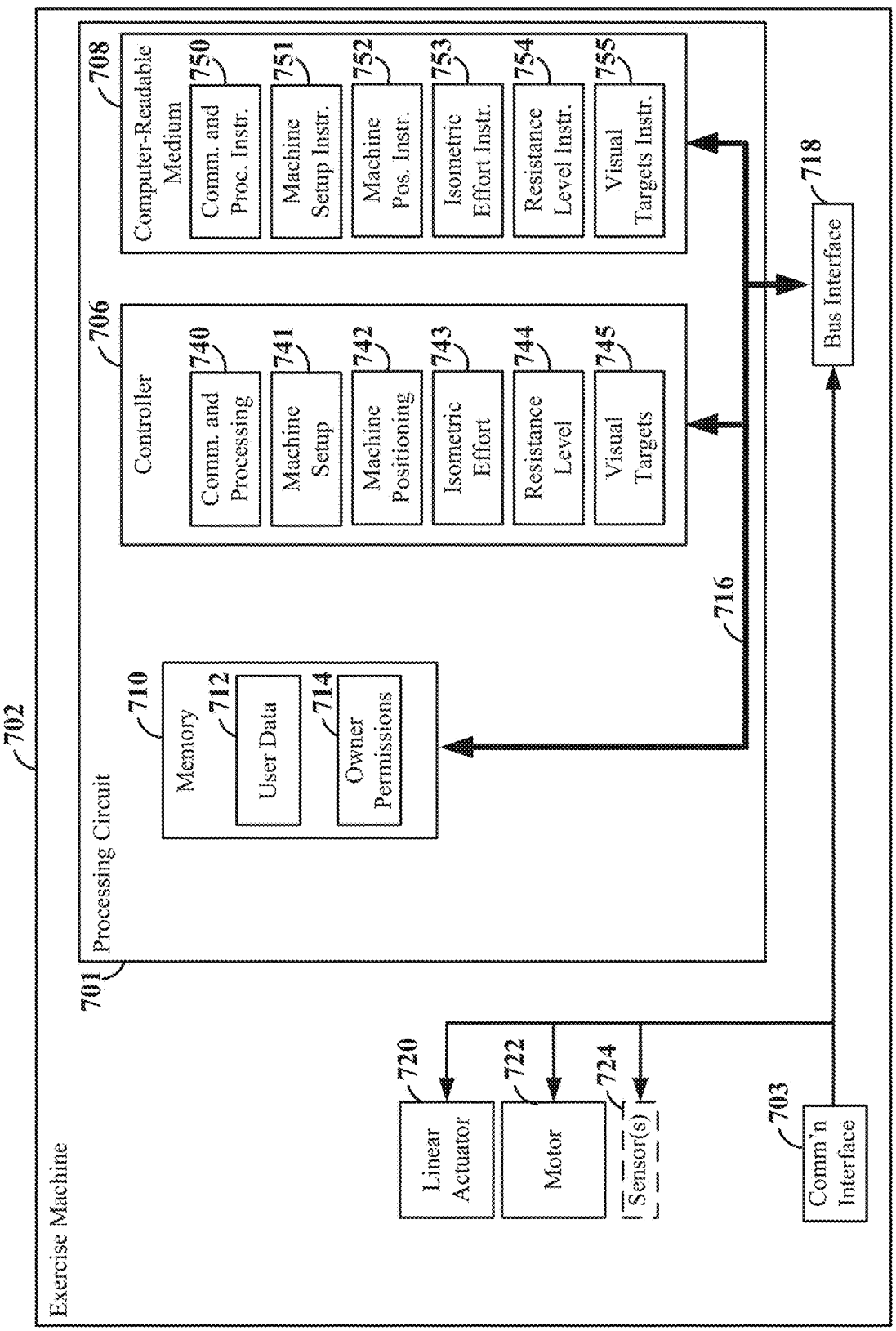
FIG. 7 illustrates a block diagram of an example hardware implementation of an exercise machine within which embodiments of the systems and methods of the present disclosure may be found.

FIG. 7 illustrates a block diagram 702 of an example hardware implementation of an exercise machine within which embodiments of the systems and methods of the present disclosure may be found. The exercise machine, having a computer system, includes a communication interface 703 connected to a bus interface 718 using a bus architecture represented generally by the bus 716. The bus 716 may communicatively couple various circuits including one or more processors (represented generally by the processing circuit 701), a memory device 710, a controller 706, and a computer readable medium 708. The bus 716 may also link various other circuits and devices, such as timing sources, peripherals, voltage regulators, and power management circuits and devices, which are well known in the art, and therefore, are not described any further.

The communication interface 703 provides a means for communicating with other apparatuses over a transmission medium. In some implementations, the communication interface 703 includes circuitry and/or programming adapted to facilitate the communication of information bi-directionally with respect to one or more communication devices in a network. In some implementations, the communication interface 703 is adapted to facilitate wireless communication of the exercise machine 702. In these implementations, the communication interface 703 may be coupled to one or more antennas (not shown) for wireless communication within a wireless communication system. In some implementations, the communication interface 703 may be configured for wire-based communication. For example, the communication interface 703 could be a bus interface, a send/receive interface, or some other type of signal interface including drivers, buffers, or other circuitry for outputting and/or obtaining signals (e.g., outputting signal from and/or receiving signals into an integrated circuit). The communication interface 703 can be configured with one or more standalone receivers and/or transmitters, as well as one or more transceivers. The communication interface 703 serves as one example of a means for receiving and/or means transmitting.

The processing circuit 701 may be responsible for managing the bus 716 and general processing, including the execution of software stored on the computer readable medium 708. The software, when executed by the processing circuit 701, may cause the processing circuit 701 to perform the various functions described below for any particular apparatus or module. The computer readable medium 708 and the memory device 710 may also be used for storing user data 712 and owner permissions 714 that is manipulated by the processing circuit 701 when executing software.

One or more processors, such as processing circuit 701 in the exercise machine 702 may execute software. Software may be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. The software may reside on a non-transient computer readable medium, such as computer readable medium 708. Non-transient computer readable medium 708 may include, by way of example, a magnetic storage device (e.g., hard disk, floppy disk, magnetic tape, magnetic strip), an optical disk (e.g., a compact disc (CD) or a digital versatile disc (DVD)), a smart card, a flash memory device (e.g., a card, a stick, or a key drive), a random access memory (RAM), a read only memory (ROM), a programmable ROM (PROM), an erasable PROM (EPROM), an electrically erasable PROM (EEPROM), a register, a removable disk, and any other suitable non-transient medium for storing software, date, and/or instructions that may be accessed and read by a computer or the processing circuit 701. Computer readable media may also include, by way of example, a carrier wave, a transmission line, and any other suitable medium for transmitting software and/or instructions that may be accessed and read by a computer or the processing circuit 701. The computer readable medium 708 may reside in the exercise machine 702, external to the exercise machine 702, or distributed across multiple entities including the exercise machine 702.

The processing circuit 702 is arranged to obtain, process and/or send data, control data access and storage, issue commands, and control other desired operations. The processing circuit 702 may include circuitry configured to implement desired programming provided by appropriate media in at least one example.

The computer readable medium 708 may be embodied in a computer program product. By way of example, a computer program product may include a computer readable medium in packaging materials. Those skilled in the art will recognize how best to implement the described functionality presented throughout this disclosure depending on the particular application and the overall design constraints imposed on the overall system.

In some aspects of the disclosure, the processing circuit 702 may include a controller 706 having circuitry configured for various functions. For example, the controller 706 may configured to manage operation of the sensors and display and to perform input/output operations associated with access to the Internet web and perform, for example, methods described herein. For example, the controller 706 may include a circuit/module for communication and processing of data 740 configured to control how data in local data storage and/or remote data storage is stored and retrieved. For example, the controller 706 may include a machine setup system/function/module/device 741 configured to control how data in local data storage and/or remote data storage is stored and retrieved. For example, the controller 708 may include a machine setup system/function/module/device 741 configured to control the exercise machine. For example, the controller 706 may include a machine positioning system/function/module/device 742 configured to adjust/position the settings of the exercise machine uniquely for each user/individual. For example, the controller 706 may include an isometric effort system/function/module/device 743 configured for the isometric exercise performed on the exercise machine. For example, the controller 706 may include a resistance level system/function/module/device 744 configured to adjust the resistance levels of the exercise machine. For example, the controller 706 may include a visual targets system/function/module/device 745 configured to identify and adjust the visual targets for the use/individual.

In some aspects of the disclosure, the non-transient computer readable medium 708 of the exercise machine 702 may include instructions that may cause the various systems/functions/modules/devices of the controller 706 to perform the methods described herein. For example, the non-transient computer readable medium 708 may include communication and processing instructions or code 750 to the circuit/module for communication and processing 740. For example, the non-transient computer readable medium 708 may include a machine setup instructions 751 corresponding to the machine setup system/function/module/device 741. For example, the non-transient computer readable medium 708 may include machine positioning instructions 752 corresponding to the machine positioning system/function/module/device 742. For example, the non-transient computer readable medium 708 may include isometric effort instructions 753 corresponding to the isometric effort system/function/module/device 743. For example, the non-transient computer readable medium 708 may include resistance level instructions 754 corresponding to the resistance level system/function/module/device 744. For example, the non-transient computer readable medium 708 may include visual targets instructions 755 corresponding to the visual targets system/function/module/device 745.

Additionally, the exercise machine utilizes a motor 722 secured to, and in electrical communication with, a linear actuator 720 having a cylinder and a piston axially engaged with the cylinder, as described above with reference to FIG. 2. Optionally, the exercise machine 702 may include one or more sensors 724 for monitoring various data during the exercise set.

Figure 8:
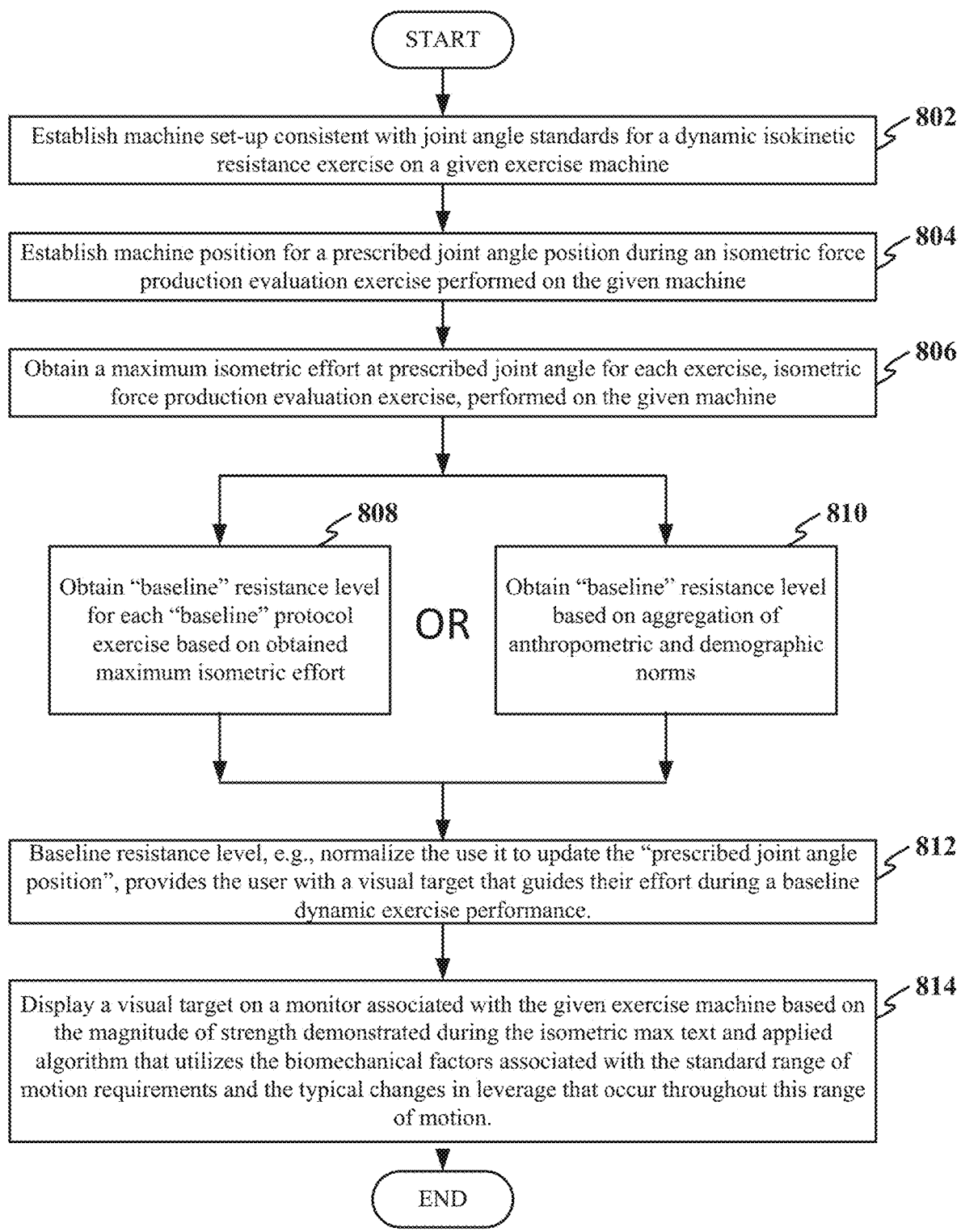
FIG. 8 illustrates a flow diagram for performing normalized isokinetic strength training performance and prescription, according to one aspect.

FIG. 8 illustrates a flow diagram for performing normalized isokinetic strength training performance and prescription according to one aspect. First, establish a machine set-up consistent with joint angle standards for a dynamic isokinetic resistance exercise on a given exercise machine 802. Next, establish a machine position for a prescribed joint angle position during an isometric force production evaluation exercise performed on the given machine 804. Next, obtain a maximum isometric effort at prescribed joint angle for each exercise, isometric force production evaluation exercise, performed on the given machine 806. A "baseline" resistance level may then be obtained. The "baseline" resistance level may be obtained or calculated for each "baseline" protocol exercise based on obtained maximum isometric effort 808 or based on aggregation of anthropometric and demographic norms 810.

Next, the baseline resistance level, e.g., normalize the use it to update the "prescribed joint angle position", provides the user with a visual target that guides their effort during a baseline dynamic exercise performance 812. The baseline exercise performance generates, through the use of an algorithm, a predicted isometric max value. This predicted isometric max value may be greater or less than the isometric max test value. The subsequent exercise effort targeting prescribed in light of this baseline predicted isometric max value and this baseline value is used as the pre-test value for progress analysis. For example, if the baseline predicted isometric max value is 100 and 1 session later the user performs an exercise set that generates a strength index value of 150, then they have achieved a gain over baseline of 50%. Because strength index normalizes performance across exercise protocols used for a given exercise movement, progress can be analyzed longitudinally (over time) even when disparate prescriptive variables (i.e., different protocols) are utilized throughout the course of time.

Next, the visual target is displayed on a monitor or screen associated with the given exercise machine based on the magnitude of strength demonstrated during the isometric max text and applied algorithm that utilizes the biomechanical factors associated with the standard range of motion requirements and the typical changes in leverage that occur throughout this range of motion. The visual target is a prescribed magnitude of effort level that varies visually throughout the movement range of motion such that visual effort targeting remains congruent with the natural changes in strength that occur throughout the range of motion 814.

Figure 9:
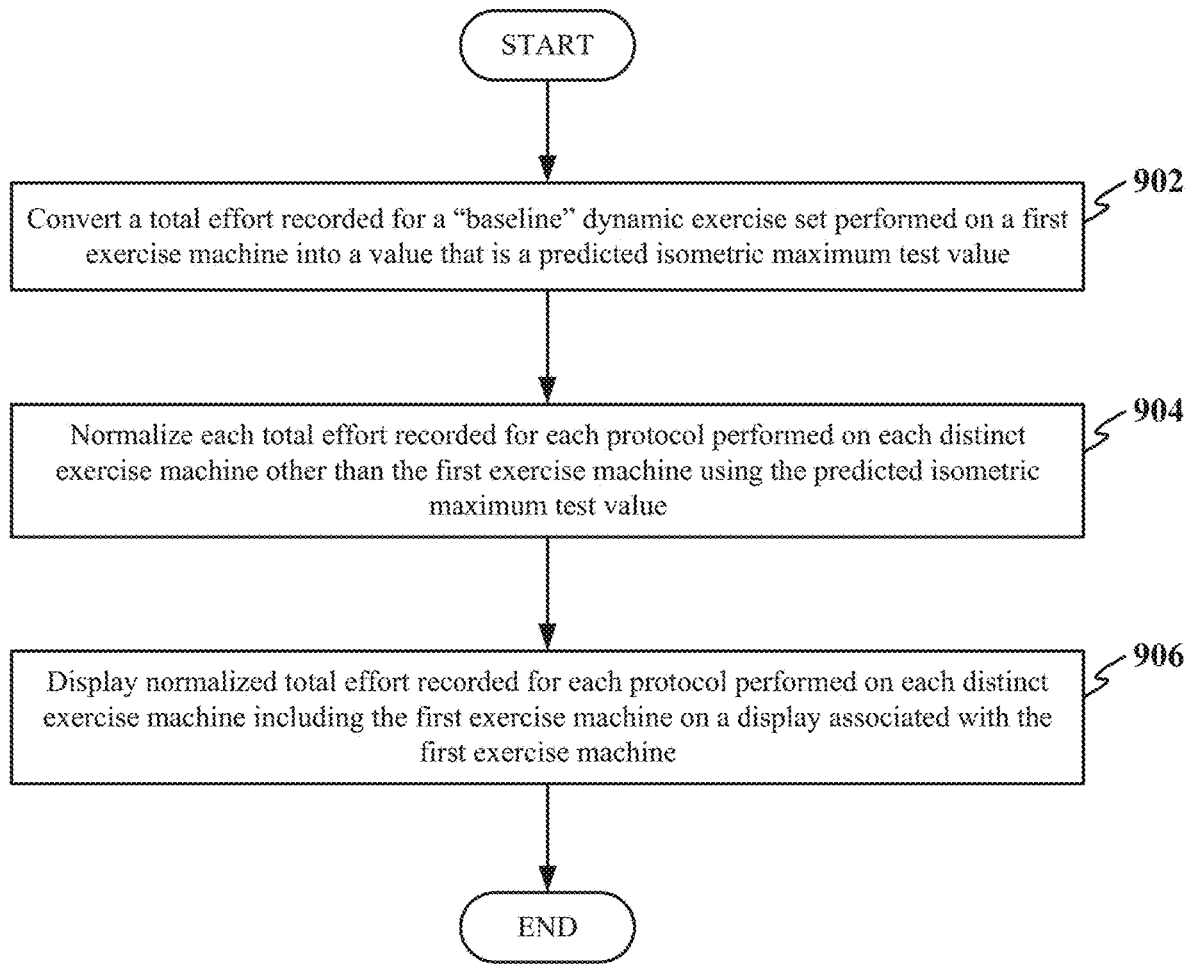
FIG. 9 illustrates a flow diagram for performing normalized isokinetic strength training performance and prescription, according to one aspect.

FIG. 9 illustrates a flow diagram for performing normalized isokinetic strength training performance and prescription according to one aspect. First, convert a total effort recorded for a "baseline" dynamic exercise set performed on a first exercise machine into a value that is a predicted isometric maximum test value 902. Total effort is a measurement of pounds (lbs.) sensed by the machines multiplied by the time that those LBS are sensed by the machines. It is not technically a measure of work as there is no acceleration. The work arm on an exercise machine moves at predetermined fixed speeds or it may remain still, and it would still measure the lbs. of effort being applied to the work arm and multiply it by the time those lbs. are exerted against it.

Next, normalize each total effort recorded for each protocol performed on each distinct exercise machine other than the first exercise machine using the predicted isometric maximum test value 904. That is, normalize each total effort for each protocol performed for a specific movement performed. Each machine is capable of one or more exercise movements. Normalization of performance is calculated to compare protocol performances for a given movement. Data is not normalized to compare different movements to each other or different machines to each other.

Display normalized total effort by way of calculating predicted isometric max value for each performance of a distinct protocol.

Next, display normalized total effort recorded for each protocol performed on each distinct exercise machine including the first exercise machine on a display or monitor associated with the first exercise machine 906.

Figure 10A:
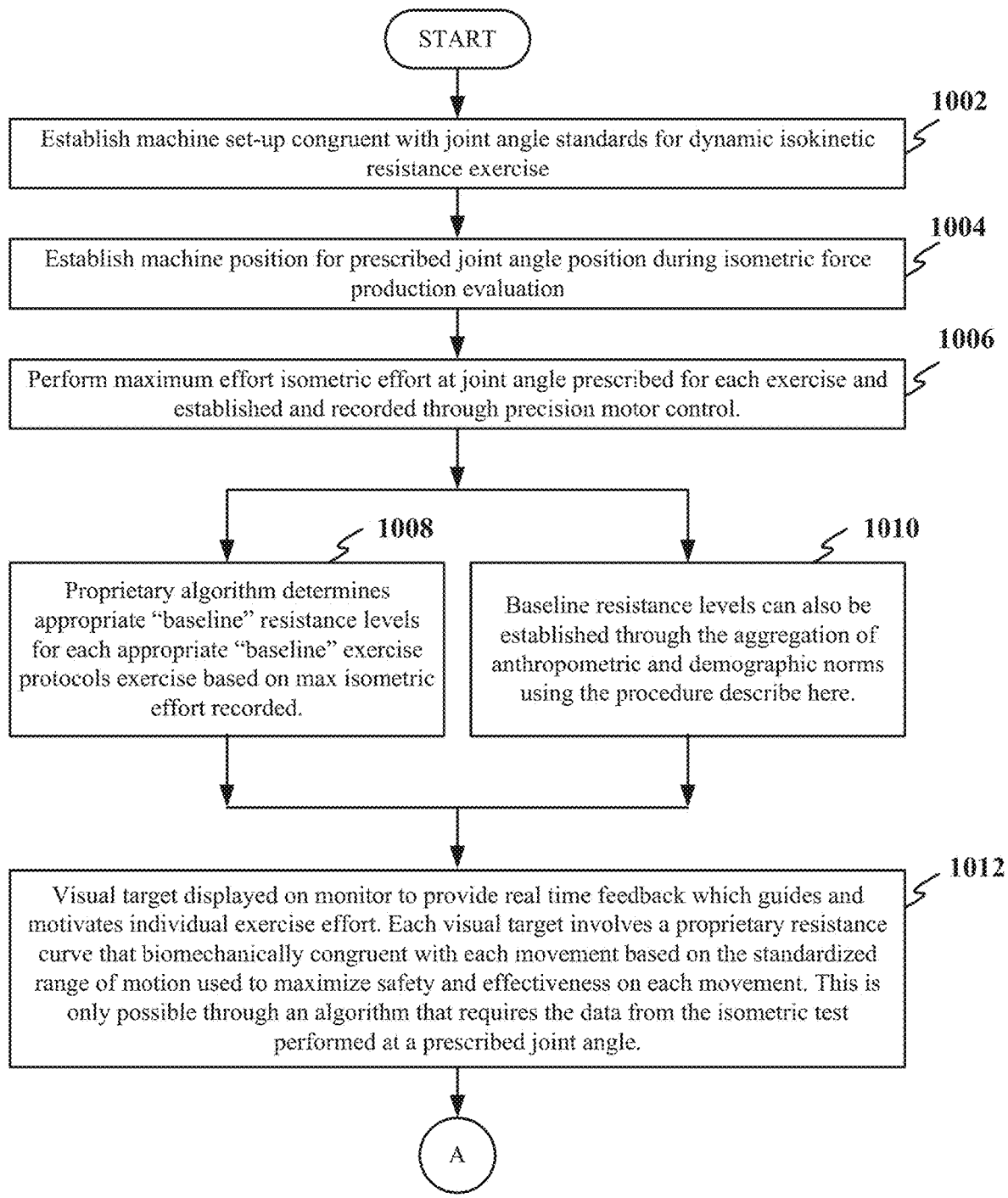
FIGS. 10A and 10B illustrate a flow diagram for performing normalized isokinetic strength training performance and prescription according to one aspect.
Figure 10B:
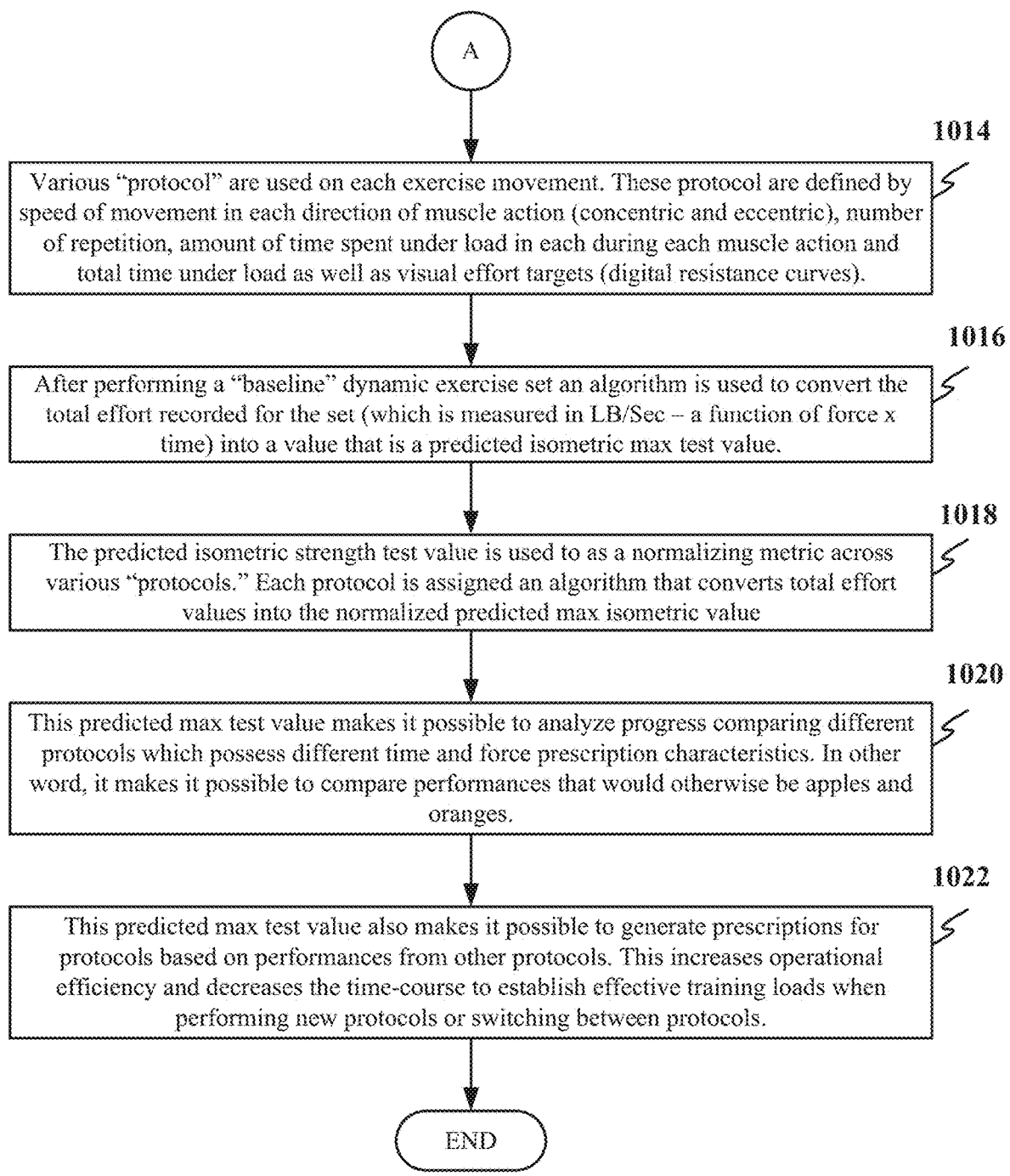

FIGS. 10A and 10B illustrate a flow diagram for performing normalized isokinetic strength training performance and prescription according to one aspect. First, establish a machine set-up congruent with joint angle standards for dynamic isokinetic resistance exercise 1002. Next, establish machine position for prescribed joint angle position during isometric force production evaluation 1004. Next, perform maximum effort isometric effort at joint angle prescribed for each exercise and established and recorded through precision motor control 1006.

Next, proprietary algorithm determines appropriate "baseline" resistance levels for each appropriate "baseline" exercise protocols exercise based on max isometric effort are recorded 1008. Next, baseline resistance levels can also be established through the aggregation of anthropometric and demographic norms using the procedure describe here 1010. Next, the visual target displayed on monitor to provide real time feedback which guides and motivates individual exercise effort. Each visual target involves a proprietary resistance curve that biomechanically congruent with each movement based on the standardized range of motion used to maximize safety and effectiveness on each movement. This is only possible through an algorithm that requires the data from the isometric test performed at a prescribed joint angle 1012.

Various "protocols" are used on each exercise movement. These protocols are defined by speed of movement in each direction of muscle action (concentric and eccentric), number of repetitions, amount of time spent under load in each during each muscle action and total time under load as well as visual effort targets (digital resistance curves) 1014. After performing a "baseline" dynamic exercise set an algorithm is used to convert the total effort recorded for the set (which is measured in LB/Sec—a function of force×time) into a value that is a predicted isometric max test value 1016.

The predicted isometric strength test value is used to as a normalizing metric across various "protocols." Each protocol is assigned an algorithm that converts total effort values into the normalized predicted max isometric value 1018. This predicted max test value makes it possible to analyze progress comparing different protocols which possess different time and force prescription characteristics. In other words, it makes it possible to compare performances that would otherwise be apples and oranges 1020. This predicted max test value also makes it possible to generate prescriptions for protocols based on performances from other protocols. This increases operational efficiency and decreases the time-course to establish effective training loads when performing new protocols or switching between protocols 1022.

According to one aspect, the results of the isometric procedure are needed to predict the appropriate effort target for the baseline protocol exercise. Alternatively, aggregated norms can be used (i.e., based on user height, weight, age, sex, lean body mass etc.)

According to one aspect, an exercise "set" is always performed using pre-designed protocols. These protocols are different combinations of prescriptive variables. Normalization of data occurs across all protocols performed for a given movement. This is possible for all the movements on all the machines.

According to one aspect, exercising using the exercise machines of the present disclosure does cause movement. The exercise machines move at a programmed speed, it is an exertion of a force or effort against a lever while that lever is in motion at a programmed speed.

According to one aspect, isometric force production exercise is performed, and maximum isometric effort is what the procedure and value are a measurement of.

According to one aspect, during an isometric procedure there is no movement. The exercise machine is at one angle and does not move while the user exerts effort against the lever.

According to one aspect, resistance levels refer to the magnitude of effort required at any point on a resistance curve. Resistance curve refers to the change across exercise range of motion that is represented by the shape of the resistance curve (the target on the screen)

According to one aspect, the user performs an exercise set at the baseline resistance level and performance is recorded and an estimated max test value is calculated and reported. This is the strength index in the field. Every subsequent exercise set performed with any protocol generates a strength index/estimated max test value.

According to one aspect, "aggregation of anthropometric and demographic norms using the procedure described herein refers to the study men and women of different ages and heights. Norms are created for the values they generate on the initial isometric procedure and/or on the baseline exercise set then these values for people are used in the age range and heights parameters.

According to one aspect, a training load is the demand placed on an individual's physiology. If it is sufficiently demanding, it stimulates muscular and systemic adaptations.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage, or mode of operation. The term "coupled" is used herein to refer to the direct or indirect coupling between two objects. For example, if object A physically touches object B, and object B touches object C, then objects A and C may still be considered coupled to one another-even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure. The terms "at least one" and "one or more" may be used interchangeably herein.

Within the present disclosure, use of the construct "A and/or B" may mean "A or B or A and B" and may alternatively be expressed as "A, B, or a combination thereof" or "A, B, or both". Within the present disclosure, use of the construct "A, B, and/or C" may mean "A or B or C, or any combination thereof" and may alternatively be expressed as "A, B, C, or any combination thereof".

One or more of the components, steps, features and/or functions illustrated herein may be rearranged and/or combined into a single component, step, feature, or function or embodied in several components, steps, or functions. Additional elements, components, steps, and/or functions may also be added without departing from novel features disclosed herein. The apparatus, devices, and/or components illustrated herein may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of:" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

As used herein, the term "determining" encompasses a wide variety of actions. For example, "determining" may include calculating, computing, processing, deriving, investigating, looking up (e.g., looking up in a table, a database or another data structure), ascertaining, and the like. Also, "determining" may include receiving (e.g., receiving information), accessing (e.g., accessing data in a memory), and the like. Also, "determining" may include resolving, selecting, choosing, establishing, and the like.

While the foregoing disclosure shows illustrative aspects, it should be noted that various changes and modifications could be made herein without departing from the scope of the appended claims. The functions, steps or actions of the method claims in accordance with aspects described herein need not be performed in any particular order unless expressly stated otherwise. Furthermore, although elements may be described or claimed in the singular, the plural is contemplated unless limitation to the singular is explicitly stated.

The invention claimed is:

1. A computer system of an exercise machine for maximizing muscle recruitment through capability based concentric and eccentric training, comprising:
   a communication interface;
   at least one processor, operatively coupled to the communication interface;
   at least one computer readable memory configured to communicate with the at least one processor, the computer readable memory having a non-transitory computer-readable storage medium configured to store instructions, that when executed by the at least one processor, configured to:

establish a machine set-up, on the exercise machine, consistent with joint angle standards for a dynamic isokinetic resistance exercise on the exercise machine;

establish a machine position, on the exercise machine, for a prescribed joint angle position during an isometric force production evaluation exercise performed on the exercise machine;

calculate a maximum isometric effort at a prescribed joint angle for one or more exercises performed on the exercise machine;

calculate a baseline resistance level for at least one protocol using a combination of data obtained from the isometric evaluation and a user performance of an exercise set on the exercise machine, wherein the baseline resistance level calculation differs from relying solely on the isometric evaluation; and convert a total effort recorded for a baseline dynamic exercise set into a predicted isometric maximum test value that is used as a normalizing metric to compare performance across different exercise protocols.

2. The system of claim 1, wherein the data includes an exercise performed, a range of motion, a duration of repetition, a duration of set, a number of repetitions, a number of sets, a tempo of repetitions, a total effort, an average effort, a peak concentric force, an average concentric force, a peak eccentric force, and an average eccentric force.

3. The system of claim 1, wherein the at least one protocol comprises one or more distinct prescriptive variables.

4. The system of claim 3, wherein the one or more distinct prescriptive variables include a time under load, a speed of movement, a concentric loading, and an eccentric loading.

5. The system of claim 1, wherein the at least one processor is further configured to normalize the data of the user performance to provide an accurate analysis of current strength levels of a user allowing for the user performance to be compared across different protocols.

6. The system of claim 1, wherein the at least one processor is further configured to display a visual target on a display screen, the visual target provides real time feedback to a user.

7. The system of claim 6, wherein the visual target is a resistance curve that is biomechanically congruent with each movement of the user based on a standardized range of motion used to maximize safety and effectiveness on the each movement.

8. The system of claim 1, wherein the at least one processor is further configured to display a normalized total effort recorded for the at least one protocol performed on the exercise machine.

9. A method of maximizing muscle recruitment through capability based concentric and eccentric training, comprising:

establishing a machine set-up, on the exercise machine, consistent with joint angle standards for a dynamic isokinetic resistance exercise on the exercise machine;

establishing a machine position, on the exercise machine, for a prescribed joint angle position during an isometric force production evaluation exercise performed on the exercise machine;

calculating a maximum isometric effort at a prescribed joint angle for one or more exercises performed on the exercise machine; and calculating a baseline resistance level for at least one protocol using a combination of data obtained from the isometric evaluation and a user performance of an exercise set on the exercise machine, wherein the baseline resistance level calculation differs from relying solely on the isometric evaluation; and converting a total effort recorded for a baseline dynamic exercise set into a predicted isometric maximum test value that is used as a normalizing metric to compare performance across different exercise protocols.

10. The method of claim 9, wherein the at least one protocol comprises one or more distinct prescriptive variables; and wherein the one or more distinct prescriptive variables include a time under load, a speed of movement, a concentric loading, and an eccentric loading.

11. The method of claim 9, further comprising displaying a visual target on a display screen, the visual target provides real time feedback to a user.

* * * * *